United States Patent
Galeazzi et al.

(12) 
(10) Patent No.: US 6,472,542 B1
(45) Date of Patent: Oct. 29, 2002

(54) METHOD FOR ALKYLATING THE ALPHA CARBON OF THE 2-METHYLBUTYRATE SECONDARY CHAIN OF LOVASTATIN

(75) Inventors: Edvige Galeazzi, Mexico City (MX); Gustavo A. Garcia, Mexico City (MX); Fernando Lara, Cuernavaca (MX); Gema Lopez, Mexico City (MX); Orestes Martinez, Mexico City (MX); Eugenio Tisselli, Mexico City (MX); Alicia Trejo, Mexico City (MX)

(73) Assignee: FERMIC S.A. de C.V., Mexico City (MX)

( * ) Notice: Subject to any disclaimer, the term of this patent is extended or adjusted under 35 U.S.C. 154(b) by 0 days.

(21) Appl. No.: 09/996,664

(22) Filed: Nov. 29, 2001

(51) Int. Cl.$^7$ .............................................. C07D 309/30
(52) U.S. Cl. ....................................... 549/292; 560/252
(58) Field of Search .......................... 549/292; 560/128, 560/252

(56) References Cited

U.S. PATENT DOCUMENTS

| | | | |
|---|---|---|---|
| 4,582,915 A | 4/1986 | Sleteinger et al. |
| 4,820,850 A | 4/1989 | Verhoeven et al. |
| 5,763,646 A | 6/1998 | Kumar et al. |
| 6,271,398 B1 | 8/2001 | Van Dalen et al. |
| 6,294,680 B1 | 9/2001 | Vries et al. |
| 6,307,066 B1 | 10/2001 | Murthy et al. |

FOREIGN PATENT DOCUMENTS

| | | | |
|---|---|---|---|
| EP | 0 137 445 B1 | 3/1990 |
| EP | 0 299 656 B1 | 12/1990 |
| ZA | 8804924 | 1/1989 |

OTHER PUBLICATIONS

European Pharmacopoeia—Supplement 2001, pp. 1403–1405.
USP 24, Official Monographs, Simvastatin, (2000), p. 1521.

*Primary Examiner*—Amelia Owens
(74) *Attorney, Agent, or Firm*—Hollander Law Firm, P.L.C.

(57) ABSTRACT

Simvastatin is produced from lovastatin in high yield and in pharmaceutical purity by forming an amide of lovastatin and protecting the free hydroxyl groups of the lovastatin amide with hexamethyidisilazane (HMDS) to form a protected lovastatin amide. The α-carbon of the 2-methylbutyrate secondary chain of the protected lovastatin amide may be methylated to form a protected simvastatin amide. The protecting groups may be removed therefrom by quenching the methylation reaction with water. The simvastatin amide which is obtained may be hydrolyzed to form simvastatin acid, followed by forming a simvastatin ammonium salt, lactonizing the salt to form simvastatin, and recrystallizing the thus formed crude Simvastatin to a high degree of purity. The HMDS protecting agent for the lactone hydroxyl groups of Lovastatin is selected so as to result in a reaction that does not produce acid so that a base, such as imidazole, is not required to neutralize the acidity of the reaction medium. Another advantage of using HMDS as a protecting agent is that the removal of the protecting agent after the methylation reaction is carried out simply, for example, by water quenching. The lactonization reaction of the present invention may be carried out using a low boiling point solvent, such as methylene chloride, in the presence of inorganic acids such as sulfuric, hydrochloric, methanesulfonic or phosphoric acid as catalyst.

28 Claims, No Drawings

METHOD FOR ALKYLATING THE ALPHA CARBON OF THE 2-METHYLBUTYRATE SECONDARY CHAIN OF LOVASTATIN

FIELD OF THE INVENTION

The present invention relates to a novel process for alkylating the alpha carbon of the 2-methylbutyrate secondary chain of lovastatin and intermediate products of the novel process, wherein the process gives a product in a high yield and in pharmaceutical purity.

BACKGROUND OF THE INVENTION

In recent years, cardiopathy has increasingly become a medical problem. This problem is associated with several factors such as diet, stress and the sedentary lifestyle of the population. One of the most important risk factors associated with coronary heart disease is the incidence of elevated cholesterol levels in plasma. Elevated cholesterol levels in plasma may cause, among other things, obstruction in the arteries and circulatory problems. See Reynolds, J. Martindale, (1993), *The Extra Pharmacopoeia*, 30$^{th}$ Edition, The Pharmaceutical Press. Cholesterol accumulation is due to both exogenous factors, such as diet, and endogenous factors, such as cholesterol production by the organism. Presently, unlike exogenous factors, cholesterol production by the organism can only be controlled by drugs that inhibit cholesterol biosynthesis.

Compounds represented by the structure (I), such as lovastatin (Ia, where R=CH$_3$) and mevastatin (Ib, where R=H), can be produced by fermentation and are well known anti-hypercholesterolaemic agents. See Republic of South Africa Patent No. 884924, to Verhoeven, T. R. and Askin, D. They act by blocking the endogenous synthesis of cholesterol through the competitive inhibition of the 3-hydroxy-3-methylglutaryl A reductase enzyme (HMG-CoA reductase).

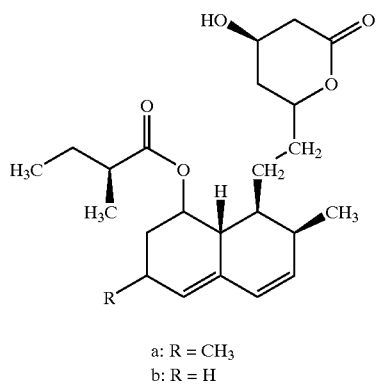

a: R = CH$_3$
b: R = H

Among several products that are prepared by semi-synthetic routes and which possess a 2,2-dimethylbutyrate secondary chain, there are compounds represented by structure (II), such as simvastatin (where R=CH$_3$). The chemical name for simvastatin is [1S-[1α, 3α, 7β, 8β (2S*, 4S*), 8aβ]]-2-2-dimethylbutanoic acid 1,2,3,7,8,8a-hexahydro-3,7-dimethyl-8-[2-(tetrahydro-4-hydroxy-6-oxo-2H-pyran-2-yl)ethyl]-1-naphthalenyl ester. Its molecular weight is 418.57 a.m.u. Simvastatin is a very active anti-hypercholesterolaemic agent that limits the biosynthesis of cholesterol by inhibiting the HMG-CoA reductase enzyme and it is widely used in the treatment of arteriosclerosis.

Products such as simvastatin are considered more potent inhibitors of HMG-CoA reductase than are their analogues with a 2-methylbutyrate chain in their structure.

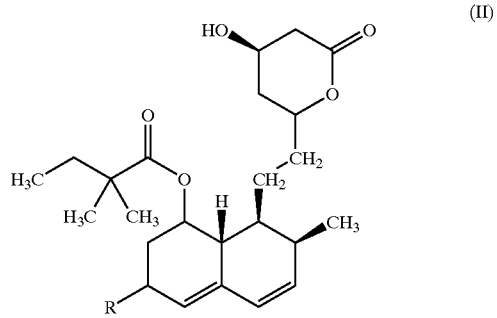

Compounds represented by structure (II) have been obtained by various routes, such as those described in U.S. Pat. Nos. 4,820,850, to Verhoeven et al., 6,271,398 B1, to Van Dalen F. et. al. and 6,294,680 B1, to Vries et al., and in European Patent No. 299,656 B1, to Verhoeven et al., wherein: (1) the lactone is hydrolyzed, (2) the OH groups of the lactone are protected, (3) the 2-methylbutyrate chain is methylated to form the 2,2-dimethylbutyrate chain, and (4) protection is removed from the lactone OH groups. However, this route is very time and labor intensive and it gives very low product yields.

Another route to alkylate the alpha carbon of the 2-methyl butyrate chain uses a metal alkyl amide and methyl iodide without hydrolyzing the lactone and without protecting the OH groups of the lactone, as described in U.S. Pat. No. 4,582,915 and in European Patent No. 137,445, both to Sletzinger et al. This procedure however presents several operative disadvantages that make it useless for production. For example, to enhance the methylation reaction, it is necessary to carry out repeated additions of the amide base and the methyl halide thereby resulting in increased impurity formation because different sites of the molecule are methylated. The yields are low and the purity of final product is under the permissible limit for use as pharmaceutical active ingredient.

In U.S. Pat. No. 4,820,850, direct methylation of the alpha carbon of the 2-methylbutyrate chain may provide a higher percentage of methylation from a single addition of the amide base and alkyl halide. However, this procedure presents some disadvantages: the protection reaction of the hydroxyl groups of the lactone using tert-butyldimethylsilyl chloride as a silylating agent is accompanied by an undesirable formation of acid. Therefore, it is essential to neutralize the acid by using a base, such as imidazole. The employment of this kind of protecting agent increases the cost of the process. Accordingly, this product is very expensive. Furthermore, this method includes an additional step to deprotect the alcohols, which is carried out in the presence of an acid, such as hydrofluoric, methanesulfonic or others, and contributes to product degradation and increased impurity formation.

In U.S. Pat. No. 6,307,066, a boronic acid is reacted with lovastatin to form a lovastatin boronate, and then the methylation of the 2-methylbutyrloxy group of lovastatin boronate provides simvastatin boronate. However, U.S. Pat. No. 6,307,066 discloses no lactone hydrolysis and no hexadimethyidisilazane protecting agent for lactone OH groups. Further, the methylation of lovastatin is quenched with aqueous acid, thereby necessitating neutralization using, for example, N$_a$HSO$_3$. Still further, in Example 1 the yield of lovastatin phenylboronate from lovastatin is low (37%).

In arriving at the method of the present invention, the present inventors have sought to avoid the above-mentioned problems. As a result, they have discovered a novel process for alkylating, preferably methylating, the alpha carbon of the 2-methylbutyrate secondary chain of lovastatin, which gives a product, such as simvastatin, in a higher yield than has been attained heretofore and in a purity acceptable for pharmaceutical use.

SUMMARY OF THE INVENTION

The present invention provides a process for methylating the alpha carbon of the 2-methylbutyrate secondary chain of lovastatin to prepare simvastatin in improved yields and in a purity desired for pharmaceutical use. In addition, the present invention provides a process for the alkylation of the alpha carbon of the 2-methylbutyrate secondary chain of lovastatin to provide compounds similar to simvastatin in improved yields. The present invention also provides intermediate and final products of the alkylation, preferably methylation, process. According to the present invention, the process for making simvastatin from lovastatin comprises forming an amide of lovastatin, thereby opening the lactone ring of the lovastatin; protecting the free hydroxyl groups of the lovastatin amide with hexamethyldisilazane (HMDS) to form a novel and unobvious protected lovastatin amide represented by structural formula (IV), given below; methylating or alkylating the α-carbon of the 2-methylbutyrate secondary chain of the protected lovastatin amide to form protected simvastatin amide and removing the protecting groups therefrom by quenching the methylation reaction with water to form simvastatin amide, represented by structural formula (V), given below; hydrolyzing the simvastatin amide to form simvastatin acid; forming a simvastatin ammonium salt in an intermediate purification step; lactonizing the salt to form simvastatin; and purifying the thus formed crude simvastatin to a high degree of purity.

In an embodiment of the present invention, a protecting agent for the lactone hydroxyl groups of lovastatin is selected so as to result in a reaction that does not produce acid. Therefore, a base, such as imidazole, is not required to neutralize the acidity of the reaction medium. This surprising result is achieved by using HMDS as a protecting agent. Another advantage of using HMDS as a protecting agent is that the removal of the protecting agent after the methylation reaction is carried out simply, for example, by water quenching, thereby eliminating a neutralization step in the removal of the protecting group and any additional steps that might be required to remove the neutralizing agent.

In another embodiment of the present invention, the lactonization reaction may be carried out using a low boiling point solvent, such as methylene chloride, in the presence of inorganic acids such as sulfuric, hydrochloric, methanesulfonic or phosphoric acid as catalyst. The lactonization reaction results in high yields of the product, e.g. simvastatin, which is represented by structure (VI):

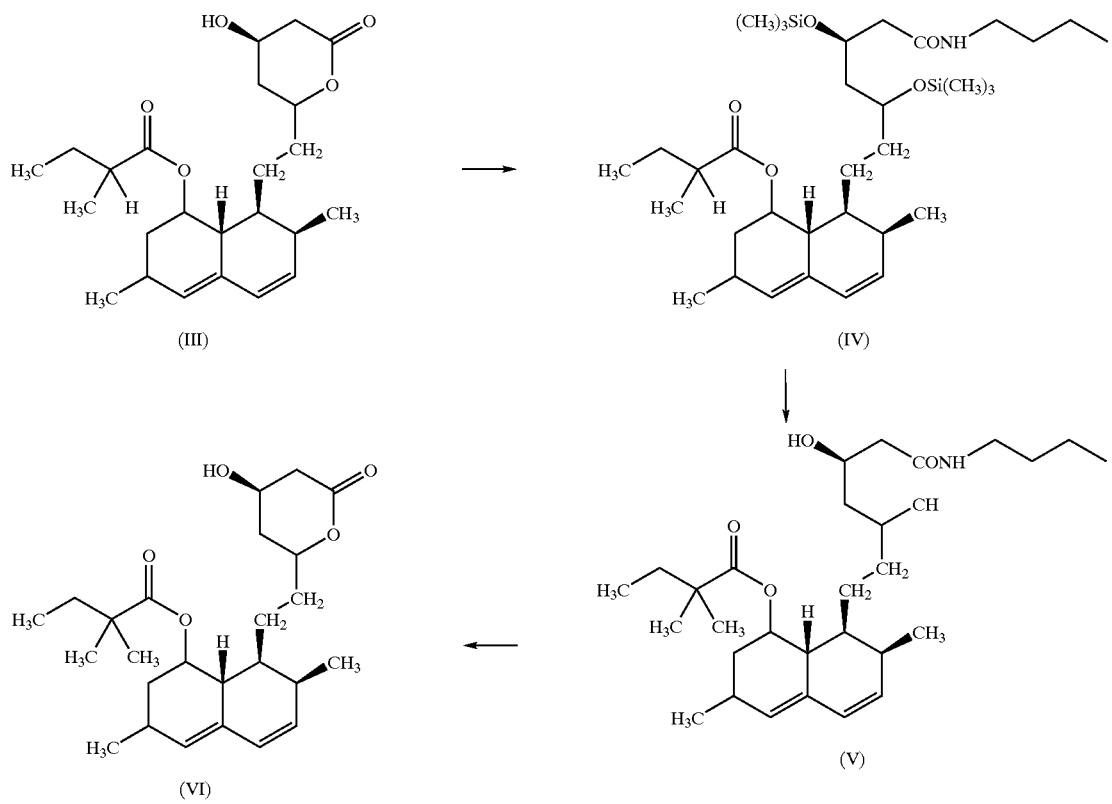

DETAILED DESCRIPTION OF THE INVENTION

The present invention comprises a novel process for alkylating, preferably methylating, the alpha carbon of the 2-methylbutyrate secondary chain of lovastatin to prepare a compound such as simvastatin in improved yields and in a purity desired for pharmaceutical use. According to the present invention, the process for making simvastatin from lovastatin comprises forming an amide of lovastatin, and thereby opening the lactone ring of the lovastatin; protecting the free hydroxyl groups of the lovastatin amide with hexamethyldisilazane (HMDS) to form a novel and unobvious protected lovastatin amide; methylating the α-carbon of the 2-methylbutyrate secondary chain of the protected lovastatin amide to form a novel and unobvious protected simvastatin amide and removing the protecting groups therefrom by quenching the methylation reaction with water; hydrolyzing the simvastatin amide to form simvastatin acid; forming a simvastatin ammonium salt in an intermediate purification step; lactonizing the salt to form simvastatin; and purifying the thus formed crude simvastatin to a high degree of purity of at least 97%, based on the weight of the dried product.

In an embodiment of the present invention, a protecting agent is selected for the lactone hydroxyl groups of lovastatin so that the protection reaction does not produce acid. Therefore, a base, such as imidazole, is not required to neutralize the acidity of the reaction medium. This surprising result is achieved by using HMDS as a protecting agent. Another advantage of using HMDS as a protecting agent is that the removal of the protecting agent after the methylation reaction may be carried out simply, by water quenching, thereby eliminating a neutralization step in the removal of the protecting group.

In another embodiment of the present invention, the lactonization reaction is carried out using a low boiling point solvent, such as methylene chloride, in the presence of inorganic acids such as sulfuric, hydrochloric, methanesulfonic or phosphoric acid as the catalyst. The lactonization reaction results in high yields of the product, e.g. simvastatin, which is represented by structure (VI).

In accordance with the present invention, lovastatin amide may be formed by reacting a proportion of about one kilogram (about 2.472 moles) of dry lovastatin, represented by structure (I), with from about 0.5 to about 1.0 liters (about 5.068 mol to about 10.136 mol), preferably from about 0.5 to about 0.75 liters, of an alkylamine, preferably n-butylamine (density 0.74 g/ml), under an inert atmosphere and under atmospheric pressure at about 45° C. to about 95° C., preferably at about 50° C. to about 70° C. Alkylamines having three or more carbon alkyl groups, preferably 3–5 carbon alkyl groups, have sufficiently low volatility to serve as both a solvent and reactant. The amidation of the lactone group of the lovastatin forms a free hydroxyl group by opening the lactone ring to form an amide of lovastatin. A second free hydroxyl group is also present on the lactone group of the lovastatin. A substantial portion of the remaining alkylamine is removed from the lovastatin amide to give a product in concentrated solution form, preferably by distillation at about 440 mm/Hg.

Following amidation, the two free hydroxyl groups of Lovastatin amide may be protected or blocked via a novel protection process. The protection process of the present invention employs hexamethyldisilazane (HMDS) to protect the free hydroxyl groups of the opened lactone ring, preferably in the absence or substantial absence of a base, such as imidazole. This process may be carried out at atmospheric pressure. The employment of hexamethyldisilazane as protecting agent avoids a neutralizing step following the removal of the protecting groups from hydroxyl groups because the protecting groups are removed with water. Therefore, it is not necessary to use a strong acid, such as hydrofluoric, methanesulfonic or other acids, which can increase product degradation and impurity formation during hydrolysis. The protection process may comprise mixing about 40 to about 60 liters of an inert organic solvent liquid solution containing about 20 kilograms (about 41.88 moles) of lovastatin amide with about 20 to about 40 liters (about 95.41 moles to about 191 moles) of hexamethyldisilazane (density 0.77 g/ml), and reacting the mixture at about room temperature and at atmospheric pressure for about 20 hours to about 48 hours. The organic solvent preferably used in the protection process of the present invention is dimethylformamide (DMF). Following the reaction, the protected lovastatin amide is then isolated and any unreacted HMDS is removed. To isolate the lovastatin amide, one volume of the protected lovastatin amide product solution is dissolved in about 2 to about 6 volumes of a hydrocarbon solvent, e.g. cyclohexane, and is then washed with about 2 to about 6 volumes of water. The organic phase is then extracted for methylation to yield about 80 to about 480 liters of a hydrocarbon solvent solution containing about 24–26 kilograms (about 38 to about 42 moles) of a protected lovastatin amide, a solution concentration of about 0.079M to about 0.525M protected lovastatin amide.

Methylation of the protected lovastatin amide may be carried out by first forming an anion according to known methods, e.g. reacting an alkali metal amide in tetrahydrofuran or another inert organic solvent with a protected lovastatin amide represented by structure (IV) which is itself dissolved in an organic solvent medium, e.g. cyclohexane, followed by adding an alkylating agent, e.g. a metallic halide, in neat form. Methylation may be carried out at atmospheric pressure. Regarding solvent proportions, a hydrocarbon solvent solution of a protected lovastatin amide (about 0.079M to about 0.525M) may be dissolved in an organic solvent medium formed mixing tetrahydrofuran solvent at a ratio of about 1 part, by volume, to about 3.5 to 8 volumes of the protected lovastatin amide solution in cyclohexane. The mixture is cooled to about –30° C. to –80° C. When cooled, the protected lovastatin amide solution (about 4.5 to about 9 parts by volume) is treated with a desired amount of alkali metal amide, contained in about 3 to about 4.5 parts, by volume of a mixture of roughly equal volumes of tetrahydrofuran and hexane at about –20° C. to about –50° C., preferably about –40° C. to about –45° C., to form an anion. The anion forming mixture is maintained at between about –20° C. to about –50° C. for about 2 to about 4 hours. Following the formation of an anion of lovastatin amide, the alkylating agent, such as a methyl halide (e.g. chloride, bromide, iodide) or methyl sulfate (e.g. mesylate, tosylate, etc.), is added at about –10° C. to –60° C., preferably at about –25° C. to about –45° C., more preferably at about –28° C. to about –32° C. Once methylation is complete, the reaction mixture is maintained at about –25° C. to about –45° C. for about 15 to about 45 minutes to prevent unwanted side reactions, such as methylation at undesired sites of the thus formed protected simvastatin amide.

The alkali metal amide used in methylation may be prepared by reacting a secondary amine, e.g. pyrrolidine, piperidine or a dialkylamine, with an n-butyl- or an n-hexyl-alkali metal compound, preferably n-hexyllithium or n-butyllithium, in an anhydrous ethereal solvent medium, e.g. tetrahydrofuran, diethyl ether or 1,2-dimethoxyethane, at a temperature of about –10° C. to –60° C., preferably about –25° C. to about –30° C. Preferably, the alkali metal amide is prepared by a combination of n-hexyllithium in a hexane solution with about an equimolar amount of pyrrolidine in a solution having about a 20% to 40%, by volume, concentration in tetrahydrofuran. When the alkali metal amide, e.g. lithium pyrrolidine, is formed it is added to an organic solvent solution of a protected lovastatin amide to form an anion by enolizing the protected lovastatin amide anion. Regarding the proportion of anion forming reactants, the amount of alkali metal amide added to the protected lovastatin amide may be about 50 moles to about 75 moles of alkali metal amide per mole of dried, protected lovastatin amide.

The methylating agent may be a methylhalide, such as methyl iodide (d=2.329 at 20° C. relative to water at 4° C). Where alkylation other than methylation is desired, for example ethylation, an ethylhalide such as ethyliodide can be used. In general, alkylating agents contain 1–3 carbon groups may be used. Regarding proportions, the amount of methyl iodide (>about 99% pure), for example, added to the protected lovastatin amide anion is about 0.25 to about 0.35 liters (about 1.8 to about 3.7 moles) per mole of dried, protected lovastatin amide. The methylation or alkylation reaction is preferably performed in an inert atmosphere, e.g. under nitrogen, in an anhydrous ethereal solvent medium, e.g. tetrahydrofuran, diethyl ether or 1,2-dimethoxyethane.

Once methylation is complete, the alcohol protecting groups may be removed from the methylated product by quenching the reaction at 10° C. or less with an excess of water or an excess of water that is contained in an aqueous liquid in an amount of water at least equal, by volume, to the amount of the organic phase present in the methylation reaction mixture to form a simvastatin amide, represented by structure (V). Quenching may be carried out in water or an aqueous liquid by adding an amount of about 1 volume of water to about 6 volumes of water per volume of reaction mixture quenched, or about 135 moles water to about 4900 moles of water per mole of protected simvastatin amide, either with or without added acid, such as 1N HCl. Preferably, quenching is carried out in the absence or substantial absence of a base. Once the reaction is quenched, the phases are separated while being kept at 10° C. or less. The organic phase may optionally be treated with about 0.7 to about 1.5 liters of a 1N solution of HCl per liter of organic phase (about 1.4 to about 20 moles of HCl per mole of protected simvastatin amide in about a 0.079M to about a 0.525M solution). The organic phase is again separated and then concentrated to about a 0.2 to about a 1.5M solution, e.g. by boiling point distillation at about 440 mm/Hg to remove tetrahydrofuran. The concentrated solution is cooled under a nitrogen atmosphere before amide hydrolysis.

The hydrolysis of simvastatin amide to form simvastatin acid may be carried out by refluxing at atmospheric pressure one part, by volume, of a concentrated solution of the amide (about 0.2 M to about 1.5 M simvastatin amide) in a mixture of about 1 part methanol, by volume, and about 1 part of a 3N solution of sodium hydroxide, by volume, for a period of about 3 to 6 hours, preferably about 4 to about 4 Y2 hours. The refluxing conditions should be sufficient to remove methanol. The amount used of each of the methanol and the 3N sodium hydroxide ranges from about 120% to about 215%, by volume, based on the volume of the concentrated solution of simvastatin amide (about 0.2 M to about 1.5 M).

An intermediate purification step may comprise the formation of a simvastatin ammonium salt from its corresponding acid and ammonium hydroxide. About one part by volume of the simvastatin acid solution from the amide hydrolysis step may be pH adjusted by 3N HCl to a pH of about 1 to about 2 and then may be extracted with about 2.5 to about 4 volumes of an organic solvent, for example, with ethyl acetate, at a temperature of about 0° C. to about 10° C. While maintaining the temperature at about 0° C. to about 10° C., preferably about 0° C. to about 5° C., the simvastatin acid may be precipitated as a crude simvastatin ammonium salt by the addition of a mixture containing 33% ammonium hydroxide and methanol in a ratio of about 1 to about 3 parts, by volume. The ammonium hydroxide and methanol mixture (about 3.14 M ammonium hydroxide) is added in the amount of about 1 liter per kilogram (about 2.377 moles) of dried, crude simvastatin acid. The precipitation mixture may be left overnight (for about 8–14 hours) at about 0° C. to about 5° C. to complete precipitation. The product may then be filtered and dried.

Lactonization is an equilibrium reaction. Several procedures have been developed in order to shift the equilibrium to lactone formation. According to the process of the present invention, this step may be carried out by distillation at atmospheric pressure at about 25° C. to about 45° C., preferably about 300° C. to about 32° C., in the presence of a low boiling point solvent, such as methyl ethyl ketone, diethyl ether, acetone, and, preferably, methylene chloride, using an inorganic acid as a catalyst, such as hydrochloric, sulfuric, methanesulfonic or phosphoric acid, in amounts of about 1 to about 3 moles of acid per kilogram of dried, crude simvastatin acid ($\geq$90% pure as determined by HPLC). The solvent is used in the amount of about 0.5 to about 1 liter per kilogram of dried, crude simvastatin acid. The procedure takes about 1–1 ½ hours and yields a more pure product than is obtained according to other lactonization methods shown in the art. The product is then washed in about 4 to 10 liters, preferably about 4 to 6 liters, of water per kilogram of dried simvastatin acid. The washed product may then be concentrated at about 440 mm/Hg and precipitated in 20–33 volumes of hexane per kilogram of dried simvastatin acid. The product may then be left overnight at about 0° C. to about 5° C. and then filtered and dried before recrystallization.

Crude simvastatin may be purified, preferably by recrystallizing it in a mixture of ethanol and water. In an embodiment of the present invention, dried crude simvastatin product is dissolved in about 4 to 6 liters ethanol per kilogram of dried, crude product and is mixed with activated charcoal, about 2% to about 5%, by weight, based on the dried crude product. The ethanolic solution is refluxed at atmospheric pressure for about 30 min. to about 60 min. and is then filtered through a filter aid precoat (Celite™). The filtrate is heated to about 40° C. to about 60° C. and about 4 to 6 liters water per kilogram dried, crude product is added. The solution is left overnight at room temperature. After recrystallization or precipitation, the product is filtered. The product is washed with a mixture of about 1–2 parts, by volume, of ethanol and about 1–2 parts, by volume, of water, preferably about 1 part by volume of each of ethanol and water. The washed product is then dried under vacuum at about 25° C. to about 70° C. to yield at least about 60–65%, by weight, based on the weight of dried lovastatin reactant, of an at least 97% pure, preferably at least 98% pure, simvastatin, by weight, based on the total weight of the product. Impurities in simvastatin can comprise fragments of simvastatin, such as various naphthalenyl dimethylbutyrates, and analogs of simvastatin, such as lovastatin and epilovastatin.

In the recrystallization step, about 4 to about 10 liters, preferably about 4 to about 6 liters, of each of the water and ethanol are added for each kilogram of dried, crude simvastatin recrystallized. In the washing step, about 8 to about 16 liters in total of the water and ethanol mixture are added for each kilogram of recrystallized Simvastatin.

The final product of the method of the present invention is obtained in a high yield and in a level of purity that consistently meets the specifications of the United States and European Pharmacopoeia. European Pharmacopoeia, for example, defines simvastatin as containing "not less than 97% and not more than the equivalent of 102.0% of (1S,3R,7S,8S,8aR)-8-[2-[(2R,4R)-4-hydroxy-6-oxotetrahydro-2H-pyran-2-yl]ethyl]-3,7-dimethyl-1,2,3,7,8,8a-hexahydronaphthalen-1-yl 2,2-dimethyl-butanoate, calculated with reference to the dried substance". See *European Pharmacopoeia—Supplement* 2001, at pages 1403–1405. United States Pharmacopoeia defines simvastatin as containing "not less than 98.0% and not more than 101.0% of $C_{25}H_{38}O_5$, calculated on the dried basis". See USP 24, Official Monographs, simvastatin, (2000), p. 1521.

In all the steps, the solutions of any intermediate, e.g the compound of structure (IVA), may be concentrated by distillation, including vacuum distillation, e.g. at about 440 mm/Hg. This reduces the amounts of solvents needed in the process of the present invention and provides a more concentrated and thus more stable compound.

In all the steps, an intermediate or product may be washed in about 4 to about 10 liters, preferably about 4 to about 6 liters, of each of water and/or methanol for each kilogram of dried reactant or intermediate from the previous step.

In all the steps, the solutions of any intermediate, e.g the compound of structure (IVA), may be purified by treatment with activated charcoal, silica gel, kieselguhr or other suitable materials. Another suitable method of purification is crystallization from a proper solvent. However, any purification step applied to an intermediate compound is necessary only for the purpose of molecular identification. Due to high conversion yields and low amounts of side products, all of the intermediate reaction steps of the present invention may be carried out in practical production substantially without the need for purification. All of the reaction steps are preferably performed under a nitrogen atmosphere and at atmospheric pressure, unless otherwise indicated.

The detailed process of the present invention may be depicted by the following reaction scheme:

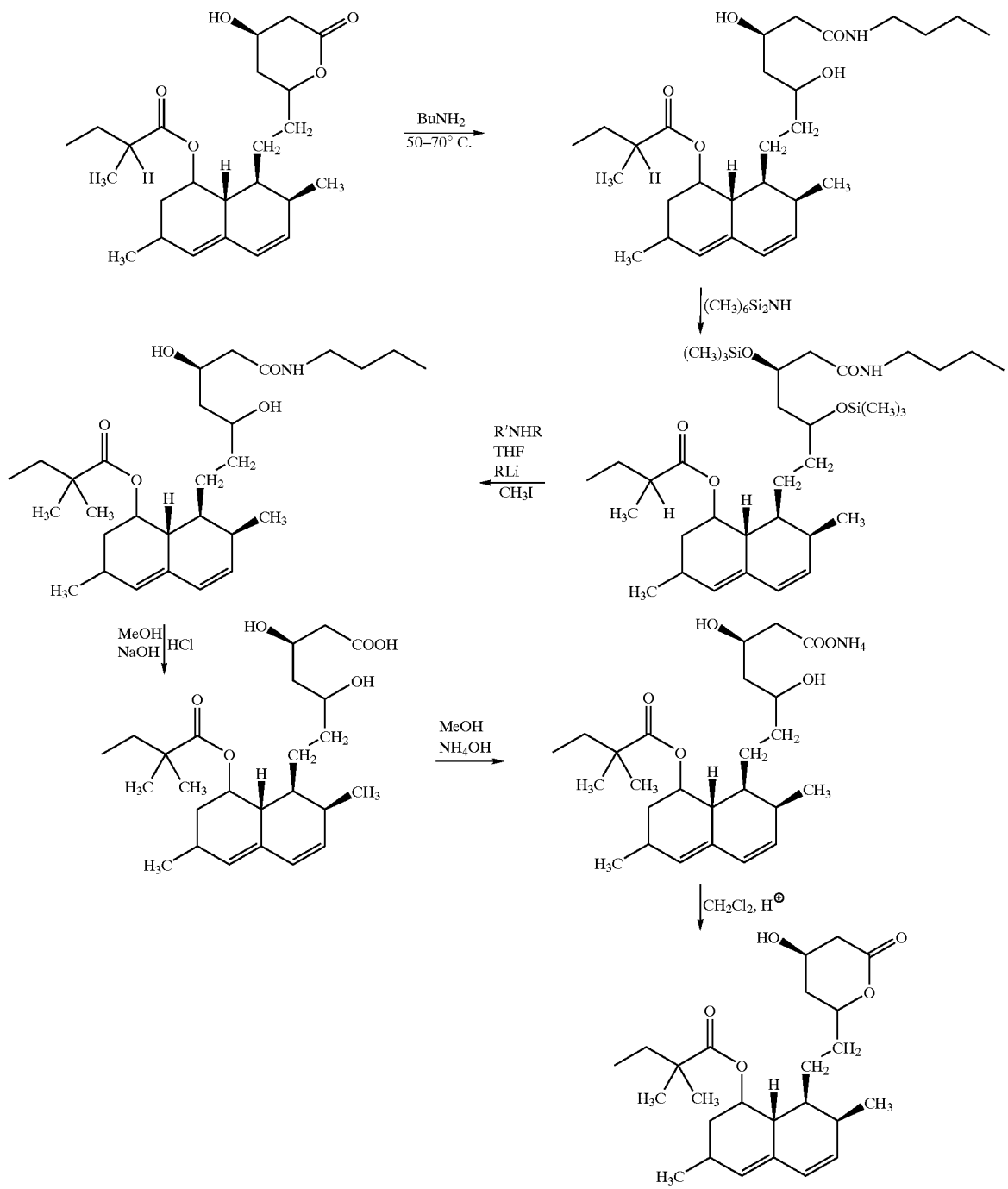

According to the reaction scheme, the starting material is lovastatin that reacts with liquid n-butylamine or another amine at about 45° C. to about 95° C. to form the corresponding lovastatin amide. Then, the free hydroxyl groups are protected by reacting lovastatin amide with a solution of hexamethyidisilazane in dimethylformamide (DMF) at about room temperature to form a compound represented by structural formula (IVA), wherein R represents a 3–5 carbon alkyl group.

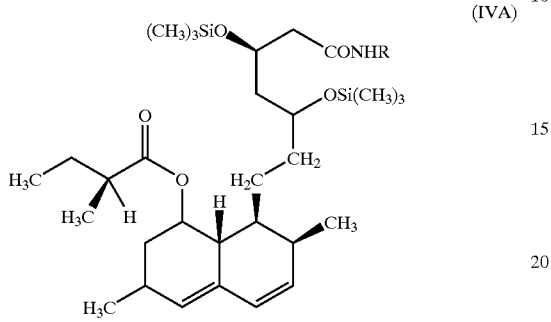
(IVA)

To perform methylation, first, an anion is formed and reacted with protected lovastatin amide to enolize the 2-carbon of the methylbutyrate chain of the protected lovastatin amide. Second, the methylating agent is reacted with the anion formed in the first reaction. To form the anion, a solution of lithium pyrrolidine is prepared by reacting pyrrolidine in anhydrous tetrahydrofuran with hexyllithium in a nitrogen atmosphere, while keeping the reaction at about −10° C. to about −60° C. The pyrrolidine and the hexyllithium are used in roughly equimolar amounts. Separately, the solution of trimethylsiloxy protected lovastatin amide in DMF is cooled to about −30° C. to about −80° C. in a nitrogen atmosphere. Then, the lithium pyrrolidine amide is added to the solution of protected Lovastatin amide to form a Lovastatin amide anion or enol, while keeping the temperature at between about −20° C. and about −50° C. The lovastatin amide anion solution is maintained at about −20° C. to about −50° C. for about 2–4 hours. A methylating agent is added to the anion solution, while keeping the temperature at from about −25° C. to about −45° C. Once the addition is finished the reaction is maintained at from about −25° C. to about −45° C. for about 15–40 minutes. The product compound is given by the structural formula (IVB), wherein R represents a 3–5 carbon alkyl group.

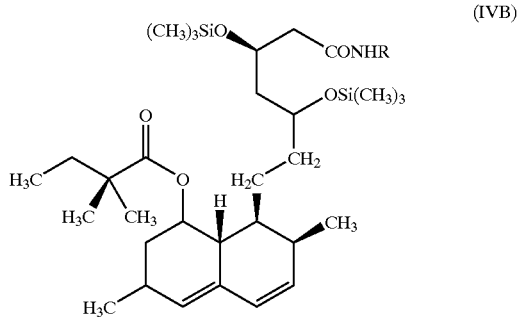
(IVB)

The methylation reaction is quenched with water and 1N hydrochloric acid. The aqueous quenching removes the trimethylsiloxy protecting groups from the free hydroxyl groups of the lactone ring by hydrolysis, thereby forming crude simvastatin amide represented by formula (VA), wherein R represents a 3–5 carbon alkyl group. The aqueous and organic phases are then separated.

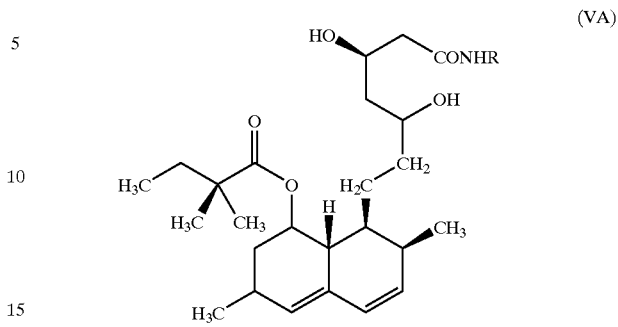
(VA)

The resulting organic phase is concentrated to remove part of the organic phase, e.g. by distillation. To this concentrate are added methanol and a 3N solution of sodium hydroxide to hydrolyze the amide group in the simvastatin amide and form a crude simvastatin sodium salt and the mixture is refluxed for about 3–6 hours, to remove methanol. The concentrated product is concentrated again, cooled to about 0° C. to about 10° C. and then the pH is adjusted to about 1 to about 2 with 3N solution of HCl to release the sodium salt formed during hydrolysis and form crude simvastatin acid. The simvastatin acid may then be converted to or precipitated as a simvastatin ammonium salt. Thus, while still cooled to about 0° C. to about 10° C., the simvastatin acid product is then extracted with ethyl acetate and precipitated as a crude simvastatin ammonium salt by the addition of a mixture of about 1 part, by volume, of ammonium hydroxide and about 3 parts, by volume, of methanol. The product is cooled overnight at about 0° C. to about 10° C. The salt is filtered and vacuum dried.

The ammonium salt is lactonized by distillation in methylene chloride (about 32° C.) in the presence of catalytic amounts of concentrated HCl (about 37% by weight in water), and the organic phase is washed with water. The organic phase is separated and the aqueous phase is discharged. Crude simvastatin is then precipitated from hexane. It is maintained overnight at about 0° C. to about 5° C. The product is filtered and vacuum dried.

The dry, crude simvastatin is dissolved in ethanol and refluxed with activated charcoal to remove ethanol, while maintaining the retentate in the form of an ethanolic solution. The ethanolic solution is filtered through a filter aid pre-coat (Celite™), heated to about 400° C. to about 60° C., and water is added. The product is crystallized overnight to reach room temperature, filtered, washed with a roughly 1:1, by volume, mixture of water and ethanol, and is then vacuum dried at about 25° C. to about 70° C. to obtain a pharmaceutical grade of purity.

The following examples are illustrative but not exhaustive of the present invention. Unless otherwise indicated, units of temperature and pressure are standard temperature and pressure, respectively, about 25° C. and about 1 atmosphere, and all proportions are calculated on a weight percent basis:

EXAMPLE 1

Preparation of Lovastatin Amide

Lovastatin (about 20 Kg) was dissolved in n-butylamine (about 10 L to about 15 L of an about 99% pure liquid) at about 45° C. to about 95° C., preferably at about 50° C. to about 70° C., until the reaction was completed. Then, the lovastatin amide solution was concentrated at about 440 mm/Hg to remove unreacted butylamine, e.g. by distillation.

EXAMPLE 2

Hydroxyl Group Protection

Dimethylformamide (DMF) (about 40 L to about 60 L) and hexamethyidisilazane (HMDS) (about 20 L to about 40 L of a liquid that is not less than 98% pure) were mixed and added to the solution of Lovastatin amide obtained in Example 1. Alternatively, the DMF can be added to the lovastatin amide and the HMDS then added to the resultant mixture. The reaction was maintained under stirring at room temperature for about 20 to about 48 hours to complete the protection reaction. The mixture was dissolved in an organic phase, cyclohexane (about 250 L to about 400 L), and was washed with water (about 250 L to about 400 L). The organic phase (about 250 L to about 400 L) was separated for use as a methylation substrate.

EXAMPLE 3

Methylation

1. Preparation of Lithium Amide

A solution of pyrrolidine (about 14 L to about 18 L, neat) in anhydrous tetrahydrofuran (THF) (about 50 L to about 70 L) was prepared under a nitrogen atmosphere. This solution was cooled to about −10° C. to about −60° C., preferably about −25° C. to about −30° C., and a 1.9M solution of hexyllithium in hexane (about 95 L to about 110 L) was added while controlling the temperature at between about −20° C. and about −50° C. Once the addition was finished, the solution was maintained at between about −20° C. and about −50° C. for about 15 min. to about 45 min. The resultant product is lithium pyrrolidine in THF.

2. Anion Formation

The solution of protected lovastatin amide in cyclohexane obtained in Example 2 and about 50 to 70 liters of anhydrous tetrahydrofuran are mixed and cooled to about −30° C. to about −80° C. under a nitrogen atmosphere. The solution of the lithium pyrrolidine from Example 1 was added to the cooled Lovastatin amide solution, while maintaining the temperature at about −20° C. to about −50° C., preferably about −40° C. to about −45° C., during the addition. The solution was maintained at this temperature for about 2 hrs. to about 4 hrs, preferably about 3 to about 3 ½ hours.

3. Methylation and Quenching

After anion formation, methyl iodide was added (about 5 L to about 7 L of a liquid that is not less than 99% pure) to the solution of lovastatin amide anion in cyclohexane and tetrahydrofuran. The temperature was maintained at about −25° C. to about −45° C., preferably about −28° C. to about −320° C., during the addition and for about 15 to 45 minutes afterward. The reaction was quenched with water (about 250 L to about 350 L). The phases were separated and the organic phase was treated with a 1N solution of HCl (about 250 L to about 350 L). The phases were separated again and the organic phase was concentrated at about 440 mm/Hg to a final volume of about 70 L to about 100 L. The concentrated simvastatin amide solution was then cooled under a nitrogen atmosphere and was reserved for amide hydrolysis and ammonium salt precipitation.

EXAMPLE 4

Amide Hydrolysis and Ammonium Salt Precipitation

To the concentrated solution of simvastatin amide obtained in Example 3 was added methanol (about 120 L to about 150 L) and a 3N solution of sodium hydroxide (about 120 L to about 150 L). The mixture was distilled to remove methanol (about 78° C.) and then was heated to reflux for about 3 hrs to about 6 hrs, preferably for about 4 hrs. to about 4½ hrs. The solution was concentrated to a volume of about 70 L to about 100 L at about 440 mm/Hg. It was cooled to about 0° C. to about 10° C. and a 3N solution of HCl was added to obtain a pH of about 1 to about 2. While being kept at about 0° C. to about 10° C., the product was extracted with ethyl acetate (about 260 L) and the ammonium salt was precipitated with about 32 liters of a mixture of 33% ammonium hydroxide and methanol in a roughly 1:3 mixture, by volume. The solution was left overnight at from about 0° C. to about 50° C. to complete the precipitation. The product, an amount of about 18 kilograms, was filtered and vacuum dried. Product yield was about 90%, based on the weight of dried lovastatin reactant.

EXAMPLE 5

Lactonization

The simvastatin acid ammonium salt obtained in Example 4 was resuspended in methylene chloride (about 10 to about 20 liters per kg of salt) and concentrated HCl (about 37%, by weight) was added (about 3 L to about 5 L). The mixture was distilled until the reaction was completed at about 25° C. to about 45° C., preferably about 30° C. to about 32° C. The total process took about 1 to 1 ½ hours. The organic phase was washed with an amount of water about equal to the amount of methylene chloride used in lactonization, was concentrated by distillation at about 440 mm/Hg to a volume of about 30 L to about 60 L, and hexane (about 450 L to about 650 L) was added to precipitate the product. The crude product was left overnight at about 0° C. to about 5° C. and was then filtered and dried under vacuum. About 15 to 16 kilograms of crude simvastatin was produced, about a 75% to 80% yield, based on the weight of dried Lovastatin reactant.

EXAMPLE 6

Final Purification

The dried crude simvastatin product obtained from the previous step was dissolved in ethanol (about 4 to about 6 volumes per kg of dried crude product), activated charcoal (about 2% to about 5% of the mixture) was added and refluxed to decolorize it for about 30 min. to about 60 min. The solution was filtered through a filter aid precoat (Celite™). The filtrate was heated to about 40° C. to about 60° C. and water was added (about 4 to about 6 volumes per kg of dried crude product). The solution was left overnight at room temperature. The product was filtered, washed with about 4 to about 6 volumes per kg of dried product of an about 1:1, by volume, mixture of ethanol and water, and dried under vacuum at about 25° C. to about 70° C.

Simvastatin was obtained in a high yield and in a pharmaceutical grade of purity which meets the United States and European Pharmacopoeia specifications. About 12 kilograms of pure simvastatin was obtained, about a 60% to about a 65% yield, based on the weight of dried lovastatin reactant.

What is claimed is:

1. A process for the preparation of simvastatin represented by structural formula (VI)

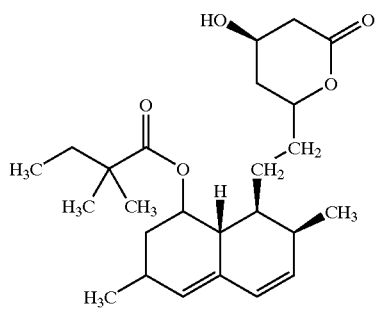

said process comprising:
- preparing a lovastatin amide by reacting lovastatin and an alkylamine,
- protecting the hydroxyl groups of said lovastatin amide by reacting said hydroxyl groups with hexamethyldisilazane (HMDS) to form a trimethylsilyl protected lovastatin amide,
- methylating by reacting a methylating agent with the alpha carbon of the 2-methylbutyrate secondary chain of said trimethylsilyl protected lovastatin amide to form a trimethylsilyl protected simvastatin amide and quenching said methylating agent with water or an aqueous liquid to remove said trimethylsilyl groups and to obtain a simvastatin amide,
- hydrolyzing said simvastatin amide to form simvastatin acid,
- converting said simvastatin acid to a simvastatin ammonium salt,
- lactonizing the simvastatin ammonium salt to form crude simvastatin, and
- purifying said crude simvastatin to form a product represented by structural formula (VI).

2. A process for the preparation of a compound of structural formula (IVA), wherein R represents a 3–5 carbon alkyl group,

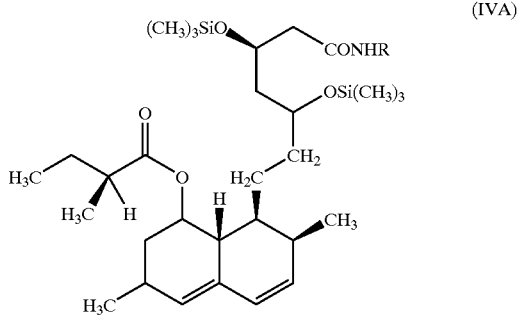

said process comprising:
- forming a lovastatin amide by reacting lovastatin and an alkylamine, and reacting said lovastatin amide with hexamethyldisilazane (HMDS) to obtain said compound of structural formula (IVA).

3. A process for the preparation of a compound of structural formula (IVA) according to claim 2, wherein said alkylamine is n-butylamine and said mixture is heated to from about 45° C. to about 95° C.

4. A process for the preparation of a compound of structural formula (IVA) according to claim 3, wherein the alkylamine and lovastatin are reacted at a temperature of about 50° C. to about 70° C.

5. A process for the preparation of simvastatin represented by structural formula (VI) as claimed in claim 1, wherein said methylating comprises reacting a methylating agent with an anion prepared by reacting lovastatin amide with a lithium amide formed by the reaction of a base comprising pyrrolidine and an alkyl lithium comprising n-hexyllithium.

6. A process as claimed in claim 5, wherein said lithium amide is formed at a temperature of about −20° C. to about −50° C.

7. A process as claimed in claim 5, wherein said lithium amide is formed at a temperature of about −250° C. to about −30° C.

8. A process as claimed in claim 5, wherein said lithium amide is lithium pyrrolidine.

9. A process for the preparation of simvastatin, represented by structural formula (VI) as claimed in claim 1, wherein said lactonizing comprises admixing said simvastatin ammonium salt with methylene chloride and a catalytic amount of an inorganic acid and refluxing to remove methylene chloride.

10. A process as claimed in claim 9 wherein said inorganic acid is hydrochloric acid.

11. A process for the preparation of simvastatin represented by structural formula (VI) as claimed in claim 1, wherein said purifying of crude simvastatin comprises adding to said crude simvastatin about 4 to about 6 liters of ethyl alcohol per kilogram of said crude simvastatin and precipitating simvastatin with about 4 to about 6 liters of water per kilogram of crude simvastatin.

12. A process for the preparation of simvastatin represented by structural formula (VI) according to claim 11, wherein said crude simvastatin is purified to an at least about 97% purity, by weight, based on the weight of said product.

13. A process as claimed in claim 1, wherein said methylating step comprises preparing a lithium amide from a base and an alkyl lithium compound followed by forming an anion by reacting said lithium amide with said protected lovastatin amide and methylating the anion to form protected simvastatin amide.

14. A process as claimed in claim 13, wherein said base is pyrrolidine and said alkyl lithium is n-hexyllithium.

15. A process as claimed in claim 13, wherein said lithium amide is formed at a temperature of about −20° C. to about −50° C.

16. A process as claimed in claim 13, wherein said lithium amide is formed at a temperature of about −25° C. to about −30° C.

17. A process as claimed in claim 13, wherein the forming of said anion comprises reacting lithium pyrrolidine at about −20° C. to about −50° C. with a solution of said protected lovastatin amide for about 2 hrs. to about 4 hrs.

18. A process as claimed in claim 17, wherein said lithium pyrrolidine is reacted at about −40° C. to about −45° C. with said solution of protected lovastatin amide for about 3 hrs. to about 3 ½ hours.

19. A process as claimed in claim 1, wherein in said methylating the methylating agent is methyl iodide and the reaction temperature is from about −25° C. to about −45° C.

20. A process according to claim 19, wherein the methylating temperature is from about −28° C. to about −32° C.

21. A process as claimed in claim 1, wherein said hydrolyzing of simvastatin amide comprises refluxing said simvastatin amide in a mixture of methanol and 3N solution of sodium hydroxide for about 3 hours to about 6 hours.

22. A process as claimed in claim 1, wherein said conversion to an ammonium salt comprises adding to simvastatin acid a mixture of about one part, by volume, of ammonium hydroxide and about three parts, by volume, of methanol, followed by precipitating the thus formed ammonium salt at from about 0° C. to about 10° C.

23. A process as claimed in claim 1 wherein said lactonizing of the simvastatin ammonium salt comprises mixing said ammonium salt with methylene chloride and a catalytic amount of an inorganic acid and distilling to remove methylene chloride.

24. A process for protecting the hydroxyl groups of lovastatin amide by reacting said hydroxyl groups with hexamethyldisilazane (HMDS).

25. A process to protect the hydroxyl groups of lovastatin amide according to claim 24, wherein said reacting is carried out in the absence of a base.

26. A process for producing a compound represented by structural formula (VA) from a compound represented by structural formula (IVA),

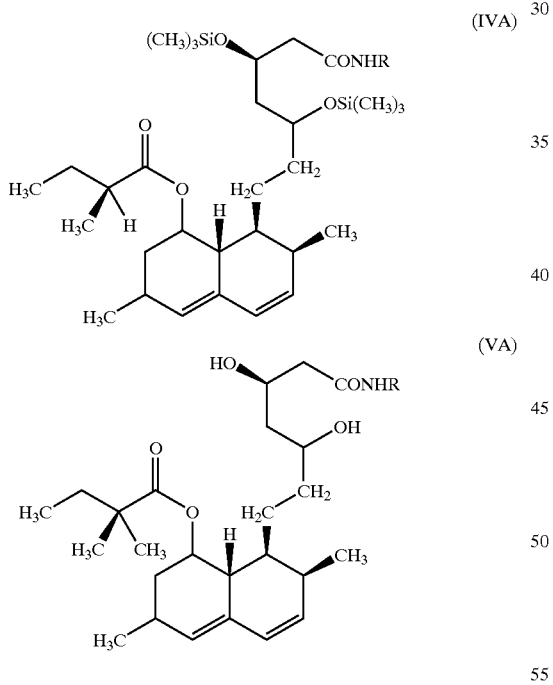

said process comprising:
  methylating the alpha carbon of the 2-methylbutyrate chain of the compound represented by structural formula (IVA) to form a compound represented by structural formula (IVB) and,

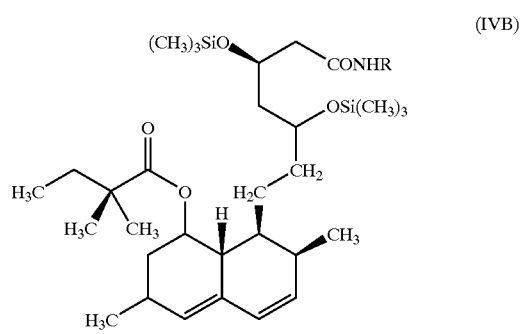

removing the trimethylsiloxy protecting groups from the compound represented by structural formula (IVB) by mixing said compound with an excess of water or an aqueous liquid to form the compound represented by structural formula (VA), wherein in each of the structural formulae (IVA), (IVB) and (VA) R represents a 3–5 carbon alkyl group.

27. A compound represented by formula (IVA), wherein R represents a 3–5 carbon alkyl group.

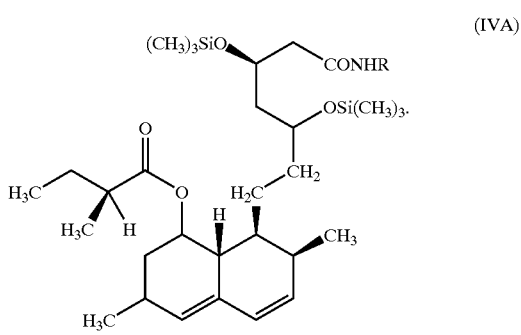

28. A protected simvastatin amide compound produced by methylating the alpha carbon of the 2-methylbutyrate secondary chain of the compound represented by structural formula (IVA), wherein R represents a 3–5 carbon alkyl group

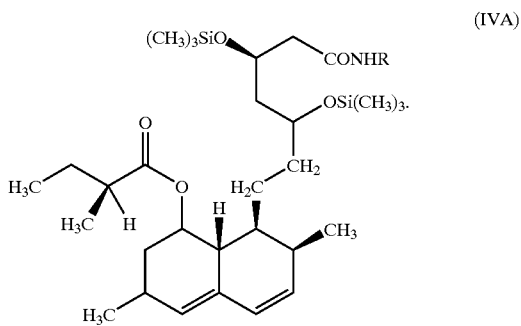

* * * * *